(12) United States Patent
Zeng et al.

(10) Patent No.: US 10,286,062 B2
(45) Date of Patent: May 14, 2019

(54) UNIVERSAL INFLUENZA VACCINE

(71) Applicant: Texas Tech University System, Lubbock, TX (US)

(72) Inventors: Mingtao Zeng, El Paso, TX (US); Junwei Li, El Paso, TX (US)

(73) Assignee: Texas Tech University System, Lubbock, TX (US)

(*) Notice: Subject to any disclaimer, the term of this patent is extended or adjusted under 35 U.S.C. 154(b) by 269 days.

(21) Appl. No.: 14/903,611

(22) PCT Filed: Jul. 9, 2014

(86) PCT No.: PCT/US2014/045839
§ 371 (c)(1),
(2) Date: Jan. 8, 2016

(87) PCT Pub. No.: WO2015/006384
PCT Pub. Date: Jan. 15, 2015

(65) Prior Publication Data
US 2016/0151480 A1    Jun. 2, 2016

Related U.S. Application Data

(60) Provisional application No. 61/844,145, filed on Jul. 9, 2013.

(51) Int. Cl.
| | | |
|---|---|---|
| *A61K 39/145* | (2006.01) | |
| *A61K 39/12* | (2006.01) | |
| *A61K 39/39* | (2006.01) | |
| *C12N 7/00* | (2006.01) | |
| *G01N 33/569* | (2006.01) | |
| *A61K 39/00* | (2006.01) | |

(52) U.S. Cl.
CPC ........... *A61K 39/145* (2013.01); *A61K 39/12* (2013.01); *A61K 39/39* (2013.01); *C12N 7/00* (2013.01); *G01N 33/56983* (2013.01); *A61K 2039/54* (2013.01); *A61K 2039/543* (2013.01); *A61K 2039/545* (2013.01); *A61K 2039/55544* (2013.01); *A61K 2039/575* (2013.01); *A61K 2039/6037* (2013.01); *A61K 2039/70* (2013.01); *C07K 2319/00* (2013.01); *C07K 2319/40* (2013.01); *C07K 2319/55* (2013.01); *C12N 2760/16122* (2013.01); *C12N 2760/16134* (2013.01); *C12N 2760/16171* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 7,238,349 B1 * | 7/2007 | D'Hondt | A61K 39/145 424/93.6 |
| 7,914,797 B2 | 3/2011 | Amon et al. | |
| 7,993,652 B2 | 8/2011 | Neirynck et al. | |

FOREIGN PATENT DOCUMENTS

| | | |
|---|---|---|
| WO | 2007066334 A1 | 4/2007 |
| WO | 2007085969 A2 | 8/2007 |
| WO | 2011120045 A1 | 9/2011 |
| WO | 2012106231 A2 | 8/2012 |
| WO | WO2012/106231 * | 8/2012 |
| WO | WO 2012/106231 * | 8/2012 |

OTHER PUBLICATIONS

De Filette et al. Virology 2005, vol. 337, pp. 149-161.*
George-Chandy et al., Infection and Immunity 2001, vol. 69, p. 5716, abstract only.*
Bommakanti G et al. "Design of an HA2-based *Escherichia coli* expressed influenza immunogen that protects mice from pathogenic challenge", Proc Natl Acad Sci U S A Aug. 3, 2010;107(31):13701-6.
Cheng VC et al. "Two Years after Pandemic Influenza A/2009/H1N1: What Have We Learned?" Clin Microbiol Rev. Apr. 2012;25(2):223-63.
De Filette M et al. "Universal influenza A vaccine: optimization of M2-based constructs", Virology. Jun. 20, 2005;337(1):149-61.
Ekiert DC et al., "Antibody recognition of a highly conserved influenza virus epitope", Science. Apr. 10, 2009;324(5924):246-51.
Feng J et al. "Influenza A virus infection engenders a poor antibody response against the ectodomain of matrix protein 2", Virol J. Dec. 6, 2006; 3:102.
Fiers W et al. "A "universal" human influenza A vaccine", Virus Res. Jul. 2004;103(1-2):173-6. Review.
Gacnik M et al. "Antibodies induced by the HA2 glycopolypeptide of influenza virus haemagglutinin improve recovery from influenza A virus infection" J Gen Virol. Apr. 2008; 89(Pt 4):958-67.
Isaka M et al., "Protective effect of nasal immunization of influenza virus hemagglutinin with recombinant cholera toxin B subunit as a mucosal adjuvant in mice". Microbiol Immunol. Feb. 2008; 52(2):55-63.
Isaka M et al. "Mucosal and systemic antibody responses against an acellular pertussis vaccine in mice after intranasal co-administration with recombinant cholera toxin B subunit as an adjuvant", Vaccine. Mar. 7, 2003;21(11-12):1165-73.
Kang SM et al. "Novel vaccines against influenza viruses," Virus Res. Dec. 2011 ; 162(1-2): 31-38.
Kingsford C et al. "2009 Swine-origin influenza A (H1N1) resembles previous influenza isolates", PLoS One. Jul. 28, 2009;4(7):e6402.

(Continued)

*Primary Examiner* — Shanon A. Foley
*Assistant Examiner* — Myron G Hill
(74) *Attorney, Agent, or Firm* — Edwin S. Flores; Daniel J. Chalker; Chalker Flores, LLP

(57) ABSTRACT

The present invention includes an isolated antigen against influenza A and a method of making the same that includes an ectodomain of influenza A Matrix Protein 2 (M2e) and a stem region of an influenza A hemagglutinin 2 (HA2) protein and an adjuvant. The invention further includes formulating the antigen into an isolated immune response stimulating fusion protein and/or a vaccine.

6 Claims, 5 Drawing Sheets
Specification includes a Sequence Listing.

(56) References Cited

OTHER PUBLICATIONS

Liu W et al. "N-terminus of M2 protein could induce antibodies with inhibitory activity against influenza virus replication", FEMS Immunol Med Microbiol. Mar. 20, 2003;35(2):141-6.
Neirynck S et al. "A universal influenza A vaccine based on the extracellular domain of the M2 protein" Nat Med. Oct. 1999;5(10):1157-63.
Sánchez-Fauquier A et al., "Isolation of cross-reactive, subtype-specific monoclonal antibodies against influenza virus HA1 and HA2 hemagglutinin subunits", Arch Virol. 1987; 97(3-4):251-65.
Staneková Z. et al., 'Conserved epitopes of influenza A virus inducing protective immunity and their prospects for universal vaccine development', Virology Journal, vol. 7, Article 351, published on Nov. 30, 2010, (online journal).
Tochikubo K et al., "Recombinant cholera toxin B subunit acts as an adjuvant for the mucosal and systemic responses of mice to mucosally co-administered bovine serum albumin", Vaccine. Jan.-Feb. 1998;16(2-3):150-5.
Vareckova E et al. "HA2-specific monoclonal antibodies as tools for differential recognition of influenza A virus antigenic subtypes", Virus Res. Mar. 2008; 132(1-2):181-6. Epub Nov. 26, 2007.
George-Chandy A. et al. "Cholera Toxin B Subunit as a Carrier Molecule Promotes Antigen Presentation and Increases CD40 and CD86 Expression on Antigen-Presenting Cells", Infection and Immunity, Sep. 2001, vol. 69, No. 9, pp. 5716-5725 [abstract].
International Search Report PCT/US2014/045839 [KIPO] dated Sep. 8, 2014.
International Preliminary Report on Patentabililty PCT/US2014/045839 [KIPO] dated Jan. 21, 2016.

\* cited by examiner

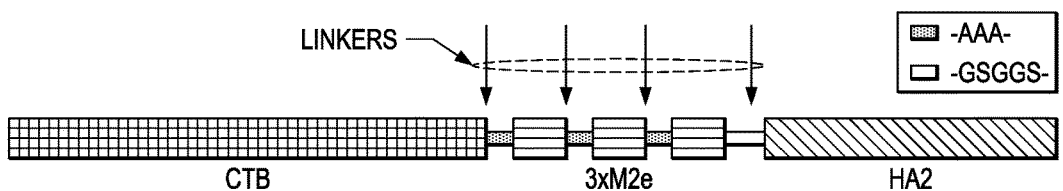
FIG. 1A
```
SLLTEVETPTRSEWECRCSDSSD    A/California/04/2009(H1N1)
SLLTEVETPIRNEWGCRCNDSSD    A/Hong Kong/1/1968(H3N2)
SLLTEVETPTRNEWECRCSDSSD    A/Viet Nam/1204/2004(H5N1)
```
FIG. 1B
```
GLFGAIAGFIEGGWTGMIDGWYGYHHQNEQGSGYA
ADQKSTQNAIDGITNKVNSVIEKMNTQFTAVGKEFN
KLEKRIENLNKKVDDGFLDIWTYNAELLVLLENERT
LDFHDSNVKNLYEKVKSQLKNNAKEIGNGCFEFYHK
CDNECMESVRNGTYDYP
```
FIG. 1C
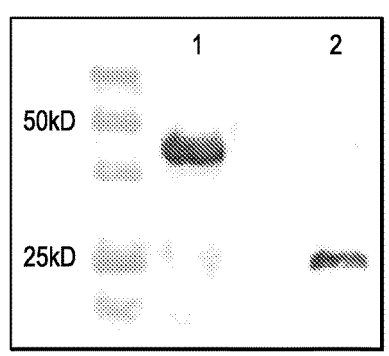
FIG. 1D
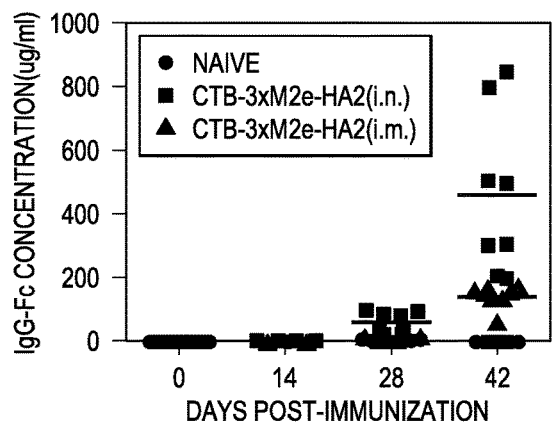
FIG. 2
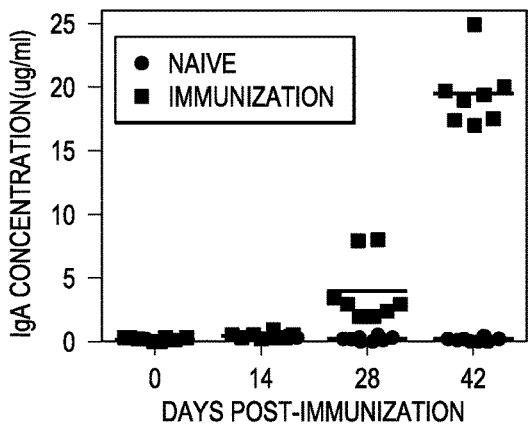
FIG. 3A

UNIVERSAL INFLUENZA VACCINE

CROSS REFERENCE TO RELATED APPLICATIONS

This application claims priority to, and is the National Phase of International Application No. PCT/2014/045839, filed on Jul. 9, 2014, which claims the benefit under 35 U.S.C. § 119(e) of U.S. Provisional Application No. 61/844,145, filed Jul. 9, 2013. All of which are hereby incorporated by reference in their entirety.

FIELD OF THE INVENTION

The present invention relates in general to the field of a novel antigen that combines at least two epitopes from influenza A, and more particularly, to an ectodomain of influenza A Matrix Protein 2 (M2e) and a stem region of an influenza A hemagglutinin 2 (HA2) protein.

BACKGROUND ART

Without limiting the scope of the invention, its background is described in connection with influenza vaccines.

In one example, U.S. Pat. No. 7,993,652, issued to Neirynck, et al., is directed to immunoprotective influenza antigen and its use in vaccination. Briefly, these inventors teach an influenza antigen that includes a fusion product with at least the extracellular part of a conserved influenza membrane protein or a functional fragment thereof and a presenting carrier, which may be a presenting (poly)peptide or a non-peptidic structure, such as glycans, peptide mimetics, or synthetic polymers. The invention is said to be a vaccine against influenza that includes at least an antigen of the invention, optionally in the presence of one or more excipients. Finally, the invention is also said to include the use of the antigen in a method for preparing the antigen and acceptor cells expressing the antigen.

U.S. Pat. No. 7,914,797, issued to Arnon, et al., and is directed to an influenza vaccine, specifically, influenza vaccines for human and veterinary use. More particularly, the invention is said to provide a vaccine capable of long term and cross-strain protection by including at least two influenza virus epitopes expressed as a chimeric polypeptide wherein at least one epitope is influenza A virus matrix protein epitope and the second epitope is a hemagglutinin peptide epitope.

SUMMARY OF THE INVENTION

The present invention includes an isolated antigen against influenza A comprising: one or more ectodomains of influenza A Matrix Protein 2 (M2e), and one or more stem regions of an influenza A hemagglutinin 2 (HA2) protein; and an adjuvant. In one aspect, the adjuvant is defined further as comprising a cholera toxin B subunit, flagellin, human papillomavirus L1 or L2 protein, herpes simplex glycoprotein D (gD), complement C4 binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles. In another aspect, the adjuvant is defined further as comprising a cholera toxin B subunit, and the cholera toxin B subunit is fused with the antigen. In another aspect, the antigen further comprises obtaining the stem region of the influenza A hemagglutinin 2 (HA2) protein from different influenza virus A strains. In another aspect, the antigen is formulated into a vaccine. In another aspect, the antigen is formulated into a vaccine further adapted for intraperitoneal, subcutaneous, intranasal, intramuscular, oral, topical or transdermal administration. In another aspect, the ectodomain of M2e is a conserved epitope of M2e. In another aspect, the antigen further comprises at least one of a pharmaceutically acceptable diluent, excipient, carrier, solubilizing agent, emulsifying agent, or preservative. In another aspect, the antigen comprises 2, 3, 4, 5, 6, 7, 8, 9, or 10 ectodomains of influenza A Matrix Protein 2 (M2e). In another aspect, the antigen comprises 2, 3, 4, 5, 6, 7, 8, 9, or 10 stem region of an influenza A hemagglutinin 2 (HA2) protein. In another aspect, the antigen comprises 3 ectodomains of influenza A Matrix Protein 2 (M2e) separated by peptide linkers.

Yet another embodiment of the present invention includes a method of making a mucosal vaccine against influenza A comprising: combining two antigens including: an ectodomain of influenza A Matrix Protein 2 (M2e) and a stem region of an influenza A hemagglutinin 2 (HA2) protein; and an adjuvant. In one aspect, the adjuvant is defined further as comprising a cholera toxin B subunit, flagellin, human papillomavirus L1 or L2 protein, herpes simplex glycoprotein D (gD), complement C4 binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles. In another aspect, the adjuvant is defined further as comprising a cholera toxin B subunit, and the cholera toxin B subunit is fused with the antigen. In another aspect, the method further comprises obtaining the stem region of the influenza A hemagglutinin 2 (HA2) protein from different influenza virus A strains. In another aspect, the antigen is formulated into a vaccine. In another aspect, the antigen is formulated into a vaccine further adapted for intraperitoneal, subcutaneous, intranasal, intramuscular, oral, topical or transdermal administration. In another aspect, the ectodomain of M2e is a conserved epitope of M2e. In another aspect, the antigen further comprises at least one of a pharmaceutically acceptable diluent, excipient, carrier, solubilizing agent, emulsifying agent, or preservative.

Yet another method of the present invention includes a method of performing a clinical trial to evaluate a candidate drug believed to be useful in immunizing against Influenza A, the method comprising: (a) measuring the immune response from a set of patients suspected of having or being exposed to influenza A; (b) administering a candidate drug to a first subset of the patients, and a placebo to a second subset of the patients, wherein the candidate drug comprises: against a fusion protein comprising an ectodomain of influenza A Matrix Protein 2 (M2e) and a stem region of an influenza A hemagglutinin 2 (HA2) protein; (c) repeating step (a) after the administration of the candidate drug or the placebo; and (d) determining if the candidate drug triggers an increase in the immune response against two or more influenza A strains that is statistically significant as compared to any increase occurring in the second subset of patients, wherein a statistically significant increase indicates that the candidate drug is useful in treating two or more strains of influenza A.

Yet another embodiment of the present invention includes an isolated immune response stimulating fusion protein against influenza A comprising: an ectodomain of influenza A Matrix Protein 2 (M2e); a stem region of an influenza A hemagglutinin 2 (HA2) protein; and cholera toxin B subunit. In another aspect, the fusion protein further comprises an adjuvant selected from at least one of flagellin, human papillomavirus L1 or L2 protein, herpes simplex glycoprotein D (gD), complement C4 binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles. In another aspect, the fusion protein further comprises obtaining the stem region of the influenza A hemagglutinin 2 (HA2) protein from different influenza virus A strains. In another aspect, the antigen is formulated into a vaccine. In another aspect, the antigen is formulated into a vaccine further adapted for intraperitoneal, subcutaneous, intranasal, intramuscular, oral, topical or transdermal administration. In another aspect, the ectodomain of M2e is a conserved epitope of M2e. In another aspect, the antigen further comprises at least one of a pharmaceutically acceptable diluent, excipient, carrier, solubilizing agent, emulsifying agent, or preservative.

DESCRIPTION OF THE DRAWINGS

For a more complete understanding of the features and advantages of the present invention, reference is now made to the detailed description of the invention along with the accompanying figures and in which:

FIGS. 1a to 1d show the design, and expression of one embodiment of the present invention in which CTB-3xM2e-HA2 or 3xM2e-HA2 chimeric protein are made. (FIG. 1a) Amino acid sequences of three M2e extracted from A/California/04/2009(H1N1)(SEQ ID NO.:1, respectively), A/Viet Nam/1204/2004(H5N1) (SEQ ID NO.:2) and A/Hong Kong/1/1968 (H3N2) (SEQ ID NO.:3); (FIG. 1b) centralized HA2 amino acid sequence (SEQ ID NO.:4); (FIG. 1c) schematic representation of chimeric CTB-3xM2e-HA2 gene sequence (SEQ ID NO.: 5). CTB, cholera toxin subunit B; M2e, matrix-2 protein ectodomain of influenza A virus; and (FIG. 1d) expressed protein CTB-3xM2e-HA2 and 3xM2e-HA2 identified by Western-blotting with anti-6xHis tag mouse monoclonal antibody.

FIG. 2 is a graph that shows the immune response to intranasal administration with protein CTB-3xM2e-HA2 induces higher level humoral (antibody) immune response than intramuscular injection with CTB-3xM2e-HA2.

FIGS. 3a to 3c show graphs with the results from intranasal administration with protein CTB-3xM2e-HA2 induces high level IgA and IgG in lung alveolar fluid of immunized Balb/c mice. (FIG. 3a) IgA level in lung alveolar fluid of Balb/c mice immunized intranasally with CTB-3xM2e-HA2; (FIG. 3b) lung alveolar fluid IgG1 levels from Balb/c mice immunized intranasally with CTB-3xM2e-HA2, and (FIG. 3c) IgG2a levels in lung alveolar fluid of Balb/c mice immunized intranasally with CTB-3xM2e-HA2.

FIGS. 4a and 4b are graphs that show the results from intranasal administration with protein CTB-3xM2e-HA2 which provided much better protection against the PR8 influenza virus (H1N1) challenge. (FIG. 4a) weight change of mouse immunized with CTB-3xM2e-HA2 or 3xM2e-HA2; and (FIG. 4b) survival rate of mouse immunized with CTB-3xM2e-HA2 or 3 xM2e-HA2.

FIGS. 5a and 5b are graphs that show the results from intranasal administration with CTB-3xM2e-HA2, which provides complete protection against pandemic 2009 H1N1 influenza virus challenge. (FIG. 5a) weight change of mouse immunized with CTB-3xM2e-HA2 or 3xM2e-HA2; and (FIG. 5b) survival rate of mouse immunized with CTB-3xM2e-HA2 or 3xM2e-HA2.

FIG. 7a shows mice were intranasally immunized with 3 doses of CTB-3xM2e-HA2. FIG. 7b shows mice were intranasally immunized with 3 doses of 3xM2e-HA2 (no antibody responses against HA2).

FIG. 8 is a graph that shows the protection induced by intranasal administration with CTB-3xM2e-HA2 against PR8 influenza virus is dose dependent. (100% protection after 3 doses of nasal vaccine).

DESCRIPTION OF THE INVENTION

Figure 3B:
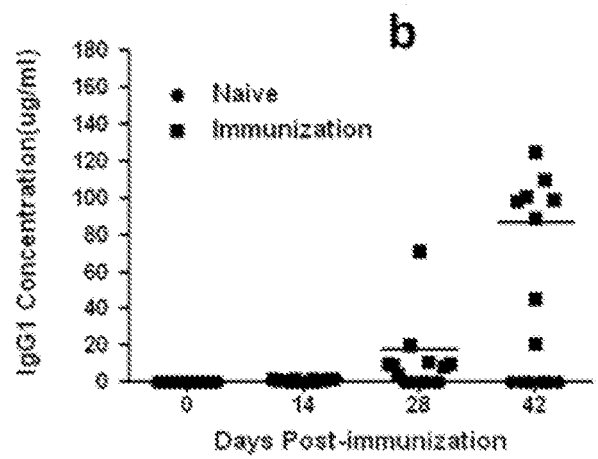

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "antigen" refers to a molecule with one or more epitopes that stimulate a host's immune system to make a secretory, humoral and/or cellular antigen-specific response against two or more strains of influenza A in a vertebrate. The term is also used interchangeably with "immunogen." In one example, the present invention includes two specific antigens that can be a complete protein, portions of a protein, peptides, fusion proteins, glycosylated proteins and combinations thereof that include an ectodomain of influenza A Matrix Protein 2 (M2e) and a stem region of an influenza A hemagglutinin 2 (HA2) protein.

For use with the present invention, one or more ectodomains of influenza A Matrix Protein 2 (M2e) and a stem region of an influenza A hemagglutinin 2 (HA2) protein antigens (native protein or protein fragment), may be provided directly or as part of a recombinant nucleic acid expression system to provide one or more antigenic ectodomain of influenza A Matrix Protein 2 (M2e) and a stem region of an influenza A hemagglutinin 2 (HA2) protein product to trigger a host immune response against two or more influenza A strains. The ectodomain of influenza A Matrix Protein 2 (M2e) and a stem region of an influenza A hemagglutinin 2 (HA2) protein antigens may be in the form of a fusion protein and may be provided to the host in the form of a DNA molecule that produces the fusion protein or the two antigens in the host.

As used herein, the term "adjuvant" refers to a substance that enhances, specifically or non-specifically, an immune response to an antigen. Non-limiting examples of adjuvants for use with the present invention include cholera toxin B subunit, flagellin, human papillomavirus L1 or L2 protein, herpes simplex glycoprotein D (gD), complement C4 binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles.

As used herein, the term "amplify", when used in reference to nucleic acids refers to the production of a large number of copies of a nucleic acid sequence by any method known in the art. Amplification is a special case of nucleic acid replication involving template specificity. Template specificity is frequently described in terms of "target" specificity. Target sequences are "targets" in the sense that they are sought to be sorted out from other nucleic acid. Amplification techniques have been designed primarily for this sorting out.

As used herein, the expressions "cell" and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations for the type and source for a cell, e.g., protozoan, prokaryotic, etc., will be clear to those of skill in the art from the designation of the cell within the context of the discussion and the examples of the present invention.

As used herein, the term "fusion protein" refers to a single protein that includes a combination of more than one protein, e.g., a single protein that includes both an ectodomain of influenza A Matrix Protein 2 (M2e) and a stem region of an influenza A hemagglutinin 2 (HA2). Another example of the present invention includes a single fusion protein that includes 2, 3, 4, 5, 6, 7, 8, 9, 10 or more individual ectodomains of influenza A Matrix Protein 2 (M2e) and/or a stem regions of an influenza A hemagglutinin 2 (HA2) in a single protein, without regard to the position of the individual protein domains or monomers. For example, the fusion protein may have, amino to carboxy, 1, 2, 3, 4 or more M2e domains, followed by 1, 2, 3, 4, or more HA2 domains, or vice versa, or interlaced, e.g., HA2-M2e-HA2-M2e, or M2e-M2e-M2e-HA2 (3xM2e-HA), or HA2-HA2-M2e-M2e (2xHA2-2xM2e), etc. All such variants are encompassed by the present invention.

As used herein, the term "gene" refers to a functional protein, polypeptide or peptide-encoding nucleic acid unit, e.g., the ectodomains of influenza A Matrix Protein 2 (M2e) and a stem region of an influenza A hemagglutinin 2 (HA2) encoding nucleic acids. As will be understood by those in the art, this functional term includes genomic sequences, cDNA sequences, probes, oligonucleotides or fragments thereof (and combinations thereof), as well as gene products, including those that may have been designed and/or altered by the user. Purified genes, nucleic acids, protein and the like are used to refer to these entities when identified and separated from at least one contaminating nucleic acid or protein with which it is ordinarily associated.

As used herein, the term "host cell" refers to cells that have been engineered to contain nucleic acid segments or altered segments, whether archeal, prokaryotic, or eukaryotic. Thus, engineered, or recombinant cells, are distinguishable from naturally occurring cells that do not have the recombinantly introduced genes. In one specific example of the present invention, the host cell has been modified by the introduction of exogenous nucleic acids that alter the expression of ectodomains of influenza A Matrix Protein 2 (M2e) and a stem region of an influenza A hemagglutinin 2 (HA2).

As used herein, the term "immunization" refers to the process of inducing a continuing protective level of antibody and/or cellular immune response, which is directed against a ectodomain of influenza A Matrix Protein 2 (M2e) and a stem region of an influenza A hemagglutinin 2 (HA2) antigen, either before or after exposure of the host to influenza A. When multiple copies of the M2e or the HA2 of the present invention are included in a construct these are designated as, e.g., when a concatenated tandem of M2e is created it can be designated 2xM2e, a trimer can be designated 3xM2e, a tetramer can be designated 4xHA2, etc., as will be readily apparent to the skilled artisan.

As used herein, the term "immunogen" refers to an antigen that is capable of initiating lymphocyte activation resulting in an antigen-specific immune response. An immunogen therefore includes any molecule that contains one or more epitopes that will stimulate a host's immune system to initiate a secretory, humoral and/or cellular antigen-specific response.

As used herein, the term "plasmids" refers to extrachromosomal, at least partially self-replicating nucleic acids. Plasmids are designated by a lower case p preceded and/or followed by capital letters and/or numbers that name the plasmid. Many plasmids are commercially available, are publicly available on an unrestricted basis, or can be constructed from such available plasmids in accord with published procedures. In addition, other equivalent plasmids are known in the art and will be apparent to the ordinary artisan.

As used herein, the term "protein-protein complex" or "protein complex" refers to an association of more than one protein. The proteins of the complex may be associated by a variety of methods, or by any combination of methods, including but not limited to functional, stereochemical, conformational, biochemical, or electrostatic association. It is intended that the term encompass associations of any number of proteins.

As used herein, the terms "protein", "polypeptide" and "peptide" refer to compounds comprising amino acids joined via peptide bonds and are used interchangeably.

As used herein, the term "vector" is used in reference to nucleic acid molecules that transfer DNA segment(s) from one cell to another. The term "vehicle" is sometimes used interchangeably with "vector." The term "vector" as used herein also includes expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes or eukaryotes usually include a promoter, an operator (optional), and a ribosome binding site, often along with other sequences. Eukaryotic cells are known to use promoters, enhancers, and termination and polyadenylation signals. The term "vector" may be used to describe the use of a carrier or other delivery system or organism to deliver the antigen(s) of the present invention to a host in order to trigger an immune response as part of a vaccine. Non-limiting examples of these vaccine vectors include viruses, bacteria, protozoans, cells (e.g., homologous or heterologous), etc., which may be live, live-attenuated, heat-killed, mechanically-killed, chemically-killed, recombinant (e.g., peptides, proteins and the like), as will be known to those skilled in the art of vaccine preparation. The skilled artisan will readily recognize the type of "vector" to which this specification and claims refer based on the description of the materials and methods used and described herein.

As used herein, the term "immunological response" refers to a composition or vaccine that includes an ectodomain of influenza A Matrix Protein 2 (M2e) and a stem region of an influenza A hemagglutinin 2 (HA2) antigen that triggers in the host a cellular- and/or antibody-mediated immune response to ectodomain of influenza A Matrix Protein 2 (M2e), and a stem region of an influenza A hemagglutinin 2 (HA2)-derived antigens. Usually, such a response may include antibody production (e.g., in the intestinal tract, from germinal centers in lymph nodes, etc.), B cell proliferation, helper T cells, cytotoxic T cell proliferation, Natural Killer activation specifically to two or more strains of influenza A itself and/or fluids, secretions, tissues, cells or hosts infected therewith.

As used herein, the terms "vaccine composition" or "vaccine" refer to an ectodomain of influenza A Matrix Protein 2 (M2e) and a stem region of an influenza A hemagglutinin 2 (HA2) antigen that is used to stimulate the immune system of a vertebrate, e.g., protection against future harm is provided by an adaptive immune response. An immune response may also be provided passively, by transferring immune protection (e.g., antibodies) from one "immunized" host to the recipient that has not been challenged by the antigen and/or is unable to generate an immune response to the antigen. An immune response may also carry from the host into the vector, wherein the antibodies that are ingested by the vector along with the parasites block parasite mating.

Seasonal influenza viruses infection infected by A or B influenza virus causes severe illness and death worldwide. The current licensed influenza vaccines mainly elicit a potent humoral immune response against hemagglutinin (HA) and Neuraminidase (NA) of seasonal influenza viruses. To cope with the slight antigen drift of seasonal influenza viruses, the annual licensed influenza vaccines need to be reformulated frequently to keep up with the mutations in HA and NA proteins. With the accumulation of mutations happened in HA and NA proteins, new influenza viruses often have been produced with the ability to escape the immunity induced by annual licensed vaccine. Sometimes there were new pandemic influenza viruses caused catastrophes without efficacious influenza vaccines. Such an instance is the 2009 Swine-Origin Influenza A viruses (H1N1), and the next influenza pandemic may be caused by H5N1 influenza viruses (Kingsford C, 2009; Cheng VC, 2012). Therefore, an urgent need is to create an effective universal influenza vaccines to prevent the future influenza pandemic disasters.

HA protein of influenza viruses is the most abundant glycosylated protein fixed on influenza virus surface. HA is synthesized as a trimerized precursor (HA0) can be cleaved by cellular proteases into HA1 and HA2. HA binding to sialic acid on target cell surface is necessary for the infection. With the pressure of specific immune response induced by seasonal vaccination, HA1 mutates with high frequency. HA2 located at the root of triple complex formed by HA1 and HA2, so HA2 with less mutation pressure is considerably more conserved than HAI. Some studies have demonstrated that HA2 specific antibody provided protection in human and mice (Bommakanti G, 2010; Varecková E, 2008; Gocník M, 2008). Monoclonal antibodies specific to highly conserved HA2 epitopes of influenza virus also have been isolated. These antibodies have the ability to recognize and neutralize several subtypes of influenza viruses and provide cross protection (Ekiert D C, 2009; Sánchez-Fauquier A, 1987). Therefore, HA2 is speculated to be a universal vaccine provide cross protection for heterologous influenza virus infection.

The ectodomain of M2 (M2e) is also highly conserved among all influenza A viruses which is generally 24 amino acids (De Filette M, 2004; Fiers W, 2004; Neirynck S, 1999), relevant sequences and portions thereof incorporated herein by reference. Because of the Conservation of M2e, it may be considered as an attractive target to induce cross-protective immune response against different influenza virus infection. However, M2e specific antibodies are almost never induced in human by natural infection of influenza viruses or experimental mice (Liu W, 2003; Feng J, 2006), therefore, an effective adjuvant is critical for immune response induced by M2e epitope.

Studies showed cholera toxin B subunit, an important mucosal adjuvant, can enhance the immune response to some mucosally administered antigens (Isaka M, 2003), relevant sequences and portions thereof incorporated herein by reference. Intranasal immunization with CTB and bovine serum albumin (BSA) or HA of influenza viruses can stimulate a high level of BSA or HA specific serum IgG antibody response and antigen specific IgA antibody response in the nasal and pulmonary lavages (Tochikubo K, 1998; Isaka M, 2008). Intranasal inactivated vaccine or subunit vaccine have the advantage over the vaccine of vaccination with the pain of injection, additionally, mucosal immune response is critical for the pathogen clearance infected by respiratory tract pathogens. For enhancing of the immune response induced by M2e and HA2, as well as to decrease the pain caused by vaccine injection with needle, M2e fused with Cholera toxin subunit and conserved HA2 as an intranasal immunogen against influenza virus was expressed. The animal experimental results show that this fused protein provided 100% protection with 100 LD50 of influenza virus challenge and it is great candidate as a universal vaccine.

Antigen design and construction of plasmid expressing CTB-3xM2e-HA2. To get a highly conserved HA2 sequence, the sequences of HA2 of 2009 pandemic H1N1 influenza viruses were aligned. Subsequently, the conserved HA2 sequence was linked with 3 matrix-2 protein ectodomains (M2e) sequences from A/California/04/2009(H1N1) SEQ ID NO.:1, A/Viet Nam/1204/2004(H5N1) SEQ ID NO.:2 and A/Hong Kong/1/1968 (H3N2) SEQ ID NO.:3 influenza viruses respectively in tandem at the N-terminal Then the DNA sequence of cholera toxin subunit B (CTB) was fused at N-terminal of 3xM2e-HA2 DNA sequence. The whole DNA sequence was $E.\ coli$ optimized and synthesis by GenScript (Piscataway, N.J.). For the expression of chimeric protein, the DNA sequence of CTB-3xM2e-HA2 was inserted into $E.\ coli$ expression vector pET200/D-TOPO (Invitrogen, Carlsbad, Calif.). The $E.\ coli$ expression plasmid carrying CTB-3xM2e-HA2 DNA sequence was named pET-CTB--3xM2e-HA2.

Expression and Purification of Protein CTB-3xM2e-HA2. BL21(DE3)strain (Invitrogen, Carlsbad, Calif.) was transformed with plasmid pET-CTB--3xM2e-HA2 and grown Luria Broth (LB) with 50 µg/ml of kanamycin until $OD_{600}$ of 0.5. The $E.\ coli$ culture was supplied with 0.1 mM Isopropyl β-D-1-thiogalactopyranoside (IPTG) and continued to culture for 4 hours at 37° C. Finally, the $E.\ coli$ cells were harvested by centrifuge at 6000 rpm for 15 minutes. The supernatant was discarded and the $E.\ coli$ cell pellets were lysed with lysis buffer (50 mM $NaH_2PO_4$, 500 mM NaCl, 10 mM imidazole, pH 8.0). Then, the lysate was centrifuged at 15,000 rpm for 30 min. The soluble fraction was moved into polypropylene columns containing Ni—NTA agarose (Qiagen, Germany) The mixture of soluble fraction with Ni—NTA agarose was incubated overnight at 4° C. After the column was washed with washing buffer (50 Mm NaH$_2$PO$_4$, 300Mm NaCl, 20 mM imidazole, pH8.0) five times, the protein binding on the Ni—NTA agarose was eluted with elution buffer (50Mm NaH$_2$PO$_4$, 300 Mm NaCl, 250 mM imidazole, pH 8.0). The purified proteins were dialyzed using the ultra centrifugal filter (Millipore, Billerica, Mass.). The eluted protein was stocked in PBS with 10% glycerol at −80° C. for the vaccination. Western-blot. Purified protein was separated on 10% SDS-PAGE, then transferred onto nitrocellulose membrane by using a semi-dry transblot apparatus (Bio-rad, Hercules, Calif.). The membrane was blocked in PBST containing 5% non-fat milk (Bio-rad, Hercules, Calif.) for 1 hour and incubated with anti-His monoclonal antibody (Invitrogen, Grand Island, N.Y.) at 4° C. overnight. After washing with PBST for 3 times, the membrane was incubated with alkaline-phosphatase conjugated goat anti-mouse Ig-G antibody at room temperature for 1 hour. After washing 3 times with PBST, the membrane was developed with substrate of BPCl/NBT (Sigma, St. Louis, Mo.).

Mice and Immunization and Challenge. 6 weeks old, specific pathogen free mice were purchased from the Jackson Laboratory, were divided into 4 groups at random and housed LYARC of Texas Tech University Health Science Center (El Paso). All studies were approved by Institutional Animal Care and Use. To test the cross-protection induced by CTB-3xM2e-HA2, 8 mice per group were bled and anesthetized with ketamine and xylazine. One group was immunized intranasally (i.n.) with Mug CTB-3xM2e-HA2, the second group was immunized intramuscularly (i.m.) with Mug CTB-3xM2e-HA2, the third group was immunized with 50 PFU PR8 influenza viruses, the fourth group was inoculated in 50 ul PBS as negative control. At 14 days and 28 days post-immunization, mice in each group were bled and boosted with previous antigen. After 2nd boost, all mice were challenged with 100•LD50 A/PR/8 influenza viruses and weighed every day.

ELISA for antibody responses. Antibody titers were tested by enzyme-linked immunosorbent assay (ELISA) with serum collected from each mouse. The 96-well plates were pre-coated 100 μl CTB-3xM2e-HA2 protein (1 μg/ml) in 50 mM sodium bicarbonate buffer (pH 9.6) overnight at 4° C., then, blocked with PBS containing 1% bovine serum albumin (BSA, Sigma) for 30 min at room temperature. 100 μl 50-fold diluted serum was added into each well and incubated overnight at 4° C. After 5 times wash, 100 ul alkaline phosphatase conjugated a-mouse IgG-Fc antibody diluted at the ratio of 1:50000 with PBS was added into each well and incubated for 1 hour at room temperature. Plates were washed with PBST 5 times and developed with 100 μl diethanolamine substrate (KPL, Gaitherburg, Md.). After incubation for 20 min, 100 μl EDTA stop solution was added into each well. The plates were read by ELISA reader (BioTek, Winooski, Vt.).

Design and expression of recombinant protein CTB-3xM2e-HA2 and 3xM2e-HA2. In this study (FIGS. 1a-d), a chimeric gene sequence was created carrying DNA sequence of cholera toxin subunit B, three M2es extracted from H1, H3 and H5 influenza subtypes (SEQ ID NO.: 1, 2, and 3) and a highly conserved HA2 gene sequence (SEQ ID NO.: 4). The optimized DNA sequence of fused protein was synthesized and the gene was inserted into E. coli expression vector pET200/D-TOPO. Subsequently, the protein fused with 6xHis tag was expressed successfully in the E. coli BL21 (DE3 strain) and purified by eluting from Ni—NAT agarose. The purified protein was confirmed by western-blotting using anti-6xHis tag mouse monoclonal antibody (Invitrogen, Grand Island, N.Y.). The result showed the molecular weight of CTB-3xM2e-HA2 is around 45kD.

Figure 3C:
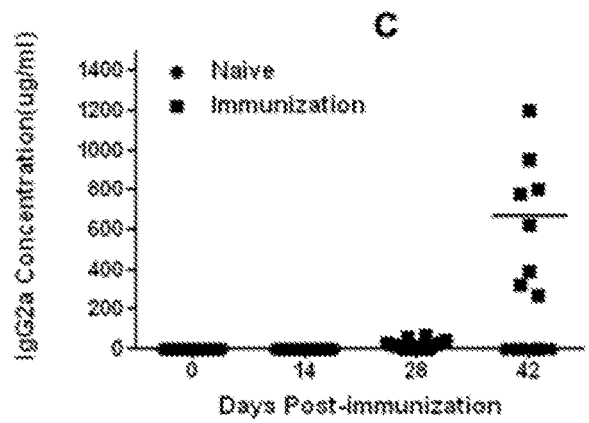

Intranasal immunization with CTB-3xM2e-HA2 induces strong humoral immunity response. There are four groups of mice under immunization. After the prime-boost immunization, the IgG-Fc concentration in the serum was tested. The results showed that in the mice immunized with CTB-3xM2e-HA2 intranasally produced higher IgG antibody that the mice immunized with CTB-3xM2e-HA2 intramuscularly (FIG. 2). After the prime immunization, the serum IgG-Fc concentration reached 2.1 μg/ml in the mice of CTB-3xM2e-HA2 intranasal immunization group. The concentration of IgG-Fc in serum of intramuscular immunization group has only 0.26 ug/ml. There is almost 10-fold difference between these two groups. After the 1st and 2n$^d$ immunization, the serum IgG-Fc concentration in in CTB-3xM2e-HA2 intrnasal immunization group attained 15ug/ml, 25ug/ml respectively. In CTB-3xM2e-HA2 intramuscular immunization group, the concentration of IgG-Fc in serum only has 3.5 μg/ml and 8.4 μg/ml. It demonstrated that cholera toxin subunit is an excellent adjuvant when vaccination is preformed intranasally. In addition, FIGS. 3a-c shows significant mucosal antibody responses after nasal immunization with the new candidate flu vaccine.

Figure 4A:
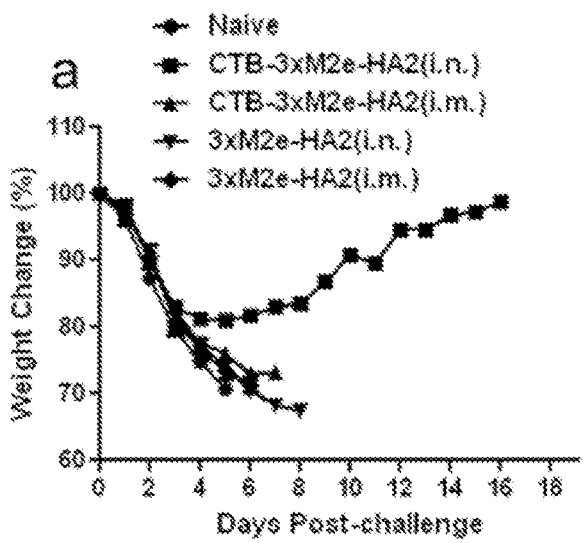
Figures 4B, 5A:
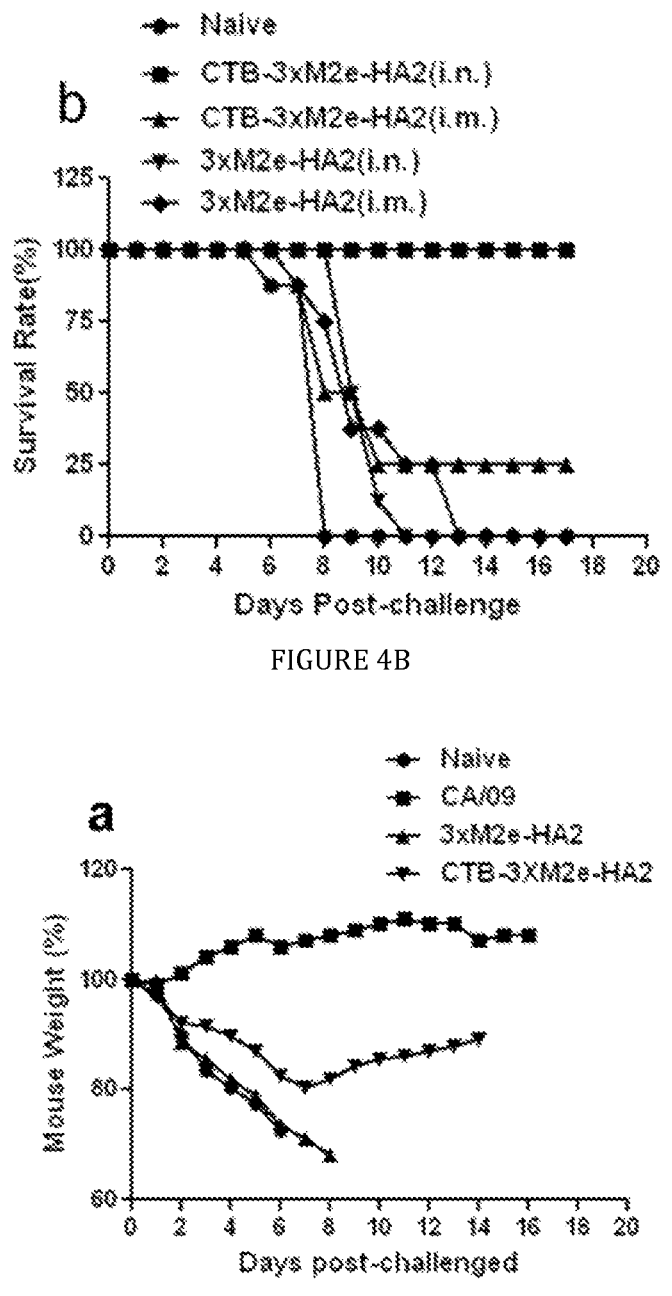
Figure 5B:
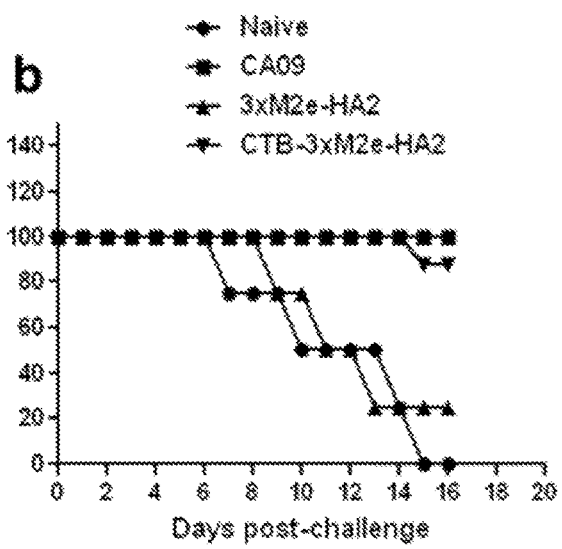
Figure 6:
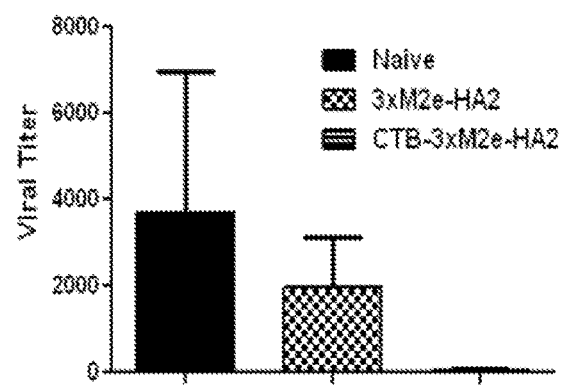
FIG. 6 is a graph that shows the results from intranasal administration with CTB-3xM2e-HA2 also provided protection against heterologous influenza virus A/HongKong/1968(H3N2) infection.
Figure 8:
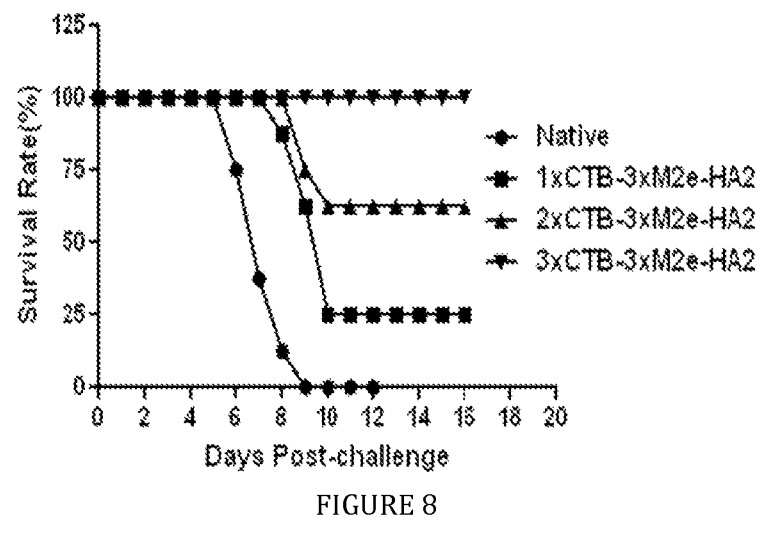

Immune response induced by CTB-3xM2e-HA2 provides protection against a heterologous influenza virus challenge (Cross-strain protective immunity). In order to test whether the recombinant CTB-3xM2e-HA2 provides cross-strain protection to the heterologous PR8 (H1N1) influenza virus, the mice were challenged with 100•LD50 PR8 influenza viruses and weighed the mice every day after challenge. All the mice in the CTB-3xM2e-HA2 intranasal immunization group were protected by the CTB-3xM2e-HA2 immunization against the lethal challenge of PR8 influenza viruses (FIGS. 4a and 4b). Weight change observed with the challenged mice indicated that the CTB-3xM2e-HA2 intranasal immunization group showed reduced weight loss compared to other groups. Weight of CTB-3xM2e-HA2 intranasal immunization group recovered completely at 16 day post-challenge. At the same time, results showed that the protection of intranasal immunization with CTB-3xM2e-HA2 is better than intramuscular immunization with CTB-3xM2e-HA2. Protective immunity shows vaccine dose dependent. Three doses of this nasal vaccine provides 100% protection against PR8 viral challenge (FIG. 8). Furthermore, three doses of this candidate nasal universal flu vaccine provide 100% protective immunity against the pandemic 2009 (H1N1) influenza virus challenge (FIGS. 5a and 5b), and against influenza A/HongKong/1968(H3N2) virus infection (FIG. 6).

Figure 7A:
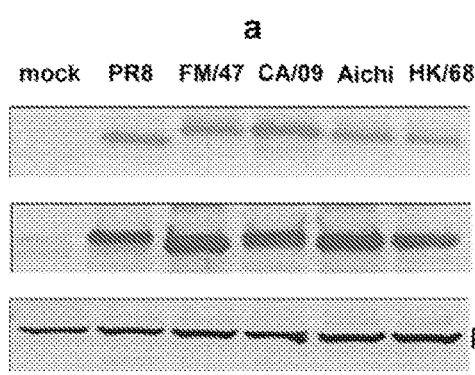
FIGS. 7a and 7b show the results for antibody induced by intranasal administration with CTB-3xM2e-HA2, which recognizes a broad panel influenza viruses (H1N1 and H3N2 strains). Results were determined by western-blotting.
Figure 7B:
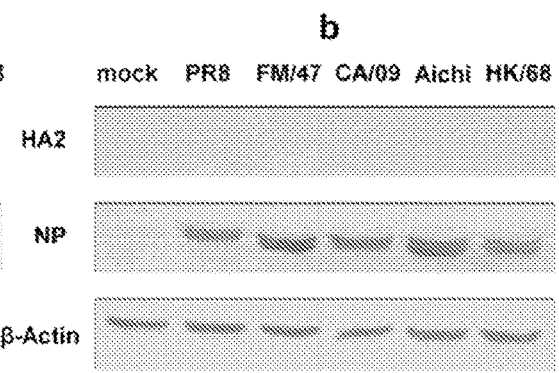

Cross-strain anti HA stem region (HA2) antibody responses elicited by nasal immunization with CTB-3xM2e-HA2. In addition, using Western-blotting assay, the antibodies elicited by nasal immunization with the candidate vaccine can cross-react with the HA2 region of HA from several influenza viruses such as PR8 (H1N1), FM/47(H1N1), CA/09 (H1N1), HK68 (H3N2), and Aichi (H3N2) strains (FIGS. 7a and 7b) was also confirmed.

In summary, the present invention provides a new universal nasal influenza vaccine that may be used to protect against future influenza epidemic, or an even more dangerous pandemic. Since the vaccine is capable of eliciting cross-strain protective immunity against influenza A viruses. It is not necessary to reformulate the vaccine annually.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Isaka M, Zhao Y, Nobusawa E, Nakajima S, Nakajima K, Yasuda Y, Matsui H, Hasegawa T, Maeyama J, Morokuma K, Ohkuma K, Tochikubo K. Protective effect of nasal immunization of influenza virus hemagglutinin with recombinant cholera toxin B subunit as a mucosal adjuvant in mice. Microbiol Immunol. 2008 Feb, 52(2):55-63.

Feng J, Zhang M, Mozdzanowska K, Zharikova D, Hoff H, Wunner W, Couch RB, Gerhard W. Influenza A virus infection engenders a poor antibody response against the ectodomain of matrix protein 2. Virol J. 2006 Dec, 6;3:102.

Bommakanti G, Citron M P, Hepler R W, Callahan C, Heidecker G J, Najar T A, Lu X, Joyce JG, Shiver J W, Casimiro D R, ter Meulen J, Liang X, Varadarajan R.

Design of an HA2-based *Escherichia coli* expressed influenza immunogen that protects mice from pathogenic challenge. Proc Natl Acad Sci USA. 2010 Aug 3, 107(31): 13701-6.

Varecková E, Mucha V, Kostolanský F, Gubareva LV, Klimov A.

HA2-specific monoclonal antibodies as tools for differential recognition of influenza A virus antigenic subtypes. Virus Res. 2008 Mar, 132(1-2):181-6. Epub 2007 Nov, 26.

Gocník M, Fislová T, Mucha V, Sládková T, Russ G, Kostolanský F, Varecková E.

Antibodies induced by the HA2 glycopolypeptide of influenza virus haemagglutinin improve recovery from influenza A virus infection. J Gen Virol. 2008 Apr, 89(Pt 4):958-67.

Ekiert DC, Bhabha G, Elsliger MA, Friesen RH, Jongeneelen M, Throsby M, Goudsmit J, Wilson I A. Antibody recognition of a highly conserved influenza virus epitope. Science. 2009 Apr, 10, 324(5924):246-51

Sánchez-Fauquier A, Villanueva N, Melero J A. Isolation of cross-reactive, subtype-specific monoclonal antibodies against influenza virus HA1 and HA2 hemagglutinin subunits. Arch Virol. 1987;97(3-4):251-65.

Isaka M, Yasuda Y, Taniguchi T, Kozuka S, Matano K, Maeyama J, Morokuma K, Ohkuma K, Goto N, Tochikubo K. Mucosal and systemic antibody responses against an acellular pertussis vaccine in mice after intranasal co-administration with recombinant cholera toxin B subunit as an adjuvant. Vaccine. 2003 Mar, 7;21(11-12):1165-73.

Tochikubo K, Isaka M, Yasuda Y, Kozuka S, Matano K, Miura Y, Taniguchi T. Recombinant cholera toxin B subunit acts as an adjuvant for the mucosal and systemic responses of mice to mucosally co-administered bovine serum albumin. Vaccine. 1998 Jan-Feb, 16(2-3):150-5.

Fiers W, De Filette M, Birkett A, Neirynck S, Min Jou W. A "universal" human influenza A vaccine. Virus Res. 2004 Jul, 103(1-2):173-6. Review.

Neirynck S, Deroo T, Saelens X, Vanlandschoot P, Jou WM, Fiers W. A universal influenza A vaccine based on the extracellular domain of the M2 protein. Nat Med. 1999 Oct, 5(10):1157-63.

Kingsford C, Nagarajan N, Salzberg S L. 2009 Swine-origin influenza A (H1N1) resembles previous influenza isolates. PLoS One. 2009 Jul, 28;4(7):e6402.

Cheng VC, To KK, Tse H, Hung IF, Yuen KY. Two Years after Pandemic Influenza A/2009/H1N1: What Have We Learned? Clin Microbiol Rev. 2012 Apr, 25(2):223-63.

Liu W, Li H, Chen YH. N-terminus of M2 protein could induce antibodies with inhibitory activity against influenza virus replication. FEMS Immunol Med Microbiol. 2003 Mar, 20;35(2): 141-6.

De Filette M, Min Jou W, Birkett A, Lyons K, Schultz B, Tonkyro A, Resch S, Fiers W. Universal influenza A vaccine: optimization of M2-based constructs. Virology. 2005 Jun, 20;337(1):149-61.

---

The invention claimed is:

1. An isolated antigen against influenza A comprising: one or more ectodomains of influenza A Matrix Protein 2 (M2e) in a fusion protein with one or more stem regions of an influenza A hemagglutinin 2 (HA2) protein and a protein adjuvant of SEQ ID NO: 4.

2. The fusion protein of claim 1, wherein the antigen is formulated into a vaccine.

3. The fusion protein of claim 1, wherein the antigen is formulated into a vaccine for intraperitoneal, subcutaneous, intranasal, intramuscular, oral, topical or transdermal administration.

4. The fusion protein of claim 1, wherein the ectodomain of M2e is a conserved epitope of M2e.

5. The fusion protein of claim 1, wherein the antigen further comprises at least one of a pharmaceutically acceptable diluent, excipient, carrier, solubilizing agent, emulsifying agent, or preservative.

6. The antigen of claim 1, further comprising obtaining the stem region of the influenza A hemagglutinin 2 (HA2) protein from different influenza virus A strains.

* * * * *

SEQUENCE LISTING

<160> NUMBER OF SEQ ID NOS: 5

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide

<400> SEQUENCE: 1

Ser Leu Leu Thr Glu Val Glu Thr Pro Thr Arg Ser Glu Trp Glu Cys
1               5                   10                  15

Arg Cys Ser Asp Ser Ser Asp
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic peptide

<400> SEQUENCE: 2

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 3
<211> LENGTH: 23
<212> TYPE: PRT
<213> ORGANISM: Artificial Sequence
<220> FEATURE:
<223> OTHER INFORMATION: Synthetic peptide

<400> SEQUENCE: 3

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 4
<211> LENGTH: 160
<212> TYPE: PRT
<213> ORGANISM: Artificial Sequence
<220> FEATURE:
<223> OTHER INFORMATION: Synthetic peptide

<400> SEQUENCE: 4

Gly Leu Phe Gly Ala Ile Ala Gly Phe Ile Glu Gly Gly Trp Thr Gly
1               5                   10                  15

Met Ile Asp Gly Trp Tyr Gly Tyr His His Gln Asn Glu Gln Gly Ser
            20                  25                  30

```
Gly Tyr Ala Ala Asp Gln Lys Ser Thr Gln Asn Ala Ile Asp Gly Ile
            35                  40                  45

Thr Asn Lys Val Asn Ser Val Ile Glu Lys Met Asn Thr Gln Phe Thr
    50                  55                  60

Ala Val Gly Lys Glu Phe Asn Lys Leu Glu Lys Arg Ile Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
                100                 105                 110

Ser Asn Val Lys Asn Leu Tyr Glu Lys Val Lys Ser Gln Leu Lys Asn
        115                 120                 125

Asn Ala Lys Glu Ile Gly Asn Phe Cys Phe Glu Phe Tyr His Lys Cys
        130                 135                 140

Asp Asn Glu Cys Met Glu Ser Val Arg Asn Gly Thr Tyr Asp Tyr Pro
145                 150                 155                 160

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Ala Ala Ala Gly Ser Gly Gly Ser
1               5
```